United States Patent
Kuhl et al.

(10) Patent No.: US 7,159,594 B2
(45) Date of Patent: Jan. 9, 2007

(54) METHOD AND DEVICE FOR ADJUSTING THE SELECTING OUT OF WINNOWINGS

(75) Inventors: Volker Kuhl, Bayreuth (DE); Heinz-Werner Masurat, Neuenmarkt (DE); Thomas Müller, Bayreuth (DE); Bernd Rabenstein, Heinersreuth (DE)

(73) Assignee: British American Tobacco (Germany) GmbH, Hamburg (DE)

( * ) Notice: Subject to any disclaimer, the term of this patent is extended or adjusted under 35 U.S.C. 154(b) by 393 days.

(21) Appl. No.: 10/654,169

(22) Filed: Sep. 3, 2003

(65) Prior Publication Data
US 2004/0040564 A1    Mar. 4, 2004

(30) Foreign Application Priority Data
Sep. 3, 2002    (DE) ............................... 102 40 617

(51) Int. Cl.
*A24C 5/32*    (2006.01)
(52) U.S. Cl. .................. 131/280; 131/905; 356/335; 356/627; 356/638; 250/559.21
(58) Field of Classification Search ........... 356/335; 382/110; 131/280, 905
See application file for complete search history.

(56) References Cited

U.S. PATENT DOCUMENTS

| | | | | |
|---|---|---|---|---|
| 4,661,985 A | * | 4/1987 | Akutsu | ..................... 382/110 |
| 6,542,234 B1 | * | 4/2003 | Ulrich et al. | ............... 356/335 |

* cited by examiner

*Primary Examiner*—Dionne W. Mayes
(74) *Attorney, Agent, or Firm*—Charles I. Sherman; Middleton Reutlinger

(57) ABSTRACT

The invention relates to a method for adjusting the selecting out of winnowings in the manufacture of smokable products, in particular cigarettes, wherein the current size distribution of a stream of tobacco particles passing a measuring point, per unit of time, is detected and compared with a settable nominal size distribution, and wherein an arrangement for separating the winnowings is continually adjusted, depending on the result of said comparison, and to a corresponding device comprising a sensor for detecting the current size distribution, an arrangement for inputting a nominal size distribution, an arrangement for comparing said current size distribution with said settable nominal size distribution, and lastly an adjusting arrangement for setting the arrangement for separating the winnowings, depending on the output signal of said comparing arrangement.

30 Claims, 4 Drawing Sheets

METHOD AND DEVICE FOR ADJUSTING THE SELECTING OUT OF WINNOWINGS

CROSS REFERENCE TO PRIOR APPLICATION

This application claims Paris Convention priority to and benefit of German Patent Application No. 102 40 617.0, filed on Sep. 3, 2002, which is incorporated herein by reference.

BACKGROUND OF THE INVENTION

1. Technical Field.

The invention relates to a method and device for adjusting the selecting out of winnowings in the manufacture of smokable products, in particular cigarettes.

2. Description of the Related Art.

For a long time it has been common in the industrial production of cigarettes to re-sift the cut tobacco before manufacturing the rod, in order to separate out larger tobacco particles, undesirable in the tobacco rod of a cigarette, which in the following shall be referred to as "winnowings".

In the case of conventional cigarettes in manufacturing machines, this sifting process is always performed in the sifter of the rod manufacturing machine. There are various techniques for separating out winnowings, which are based primarily on the different masses of the winnowings on the one hand, and the tobacco lamina desired in the cigarette—in the following called lamina for short—on the other.

The essence of the common methods is that the tobacco particles are spatially divided into light and heavy particles by the effect of gravity and/or an additional force, e.g. an influencing stream of air.

A known separating technique is described in DE-PS 11 57 523, in which tobacco particles mechanically ejected by a Winnover cylinder pass through different trajectories, strike two impact metal sheets and are thus separated.

In the method as set forth in GB-PS 971 736, tobacco particles are propelled through a stream of air, whereby the lighter particles are pulled along and the heavier particles fall down onto a sieve. A stream of air flowing through the sieve from below can again separate the lighter particles from the heavier ones.

GB-PS 998 476 shows a method in which the tobacco particles fall in a continuous stream through a stream of air introduced transversely. The tobacco particles are deflected to different degrees due to their different masses and are thus separated.

In the method as set forth in DE-PS 11 67 241, tobacco particles are accelerated by a casting-off cylinder and pass through different trajectories due to their mass. The heavier tobacco particles, generally the stems, fall into a stem box. The lighter tobacco particles fall through a transverse or reverse sifting stream of air, which separates the heavier particles still present from the lighter ones.

U.S. Pat. No. 3,092,117 shows tobacco particles being pneumatically conveyed in a first stream of air. A second stream of air deflects the lighter particles and thus separates two fractions from each other.

U.S. Pat. No. 3,173,861 shows tobacco particles falling down into an adjustable stream of air substantially perpendicular to the falling direction. The heavier particles are not deflected or hardly deflected and so reach a lower collecting opening. Adjustment is provided in the sense that the basic settings of the machine can be changed, so as to adjust the separation method to different tobaccos.

DE-PS 21 06 134 shows a method in which tobacco particles are guided past a suction cylinder, such that lighter particles remain stuck to the suction cylinder while heavier particles fall downwards. For the basic settings of the separating mechanism, two different air supplies are provided.

Lastly, DE 42 42 325 A1 shows a method in which tobacco particles are separated from each other in a cyclone separator.

If the separated material separated using one of the methods as set forth in the prior art is examined by weighing and sieving the separated out material collected over a certain period of time, this reveals that—depending on the setting of the separating process—winnowings and lamina are almost always present in different quantities. Using an optimum setting, however, it should be possible to separate all the winnowings but none of the lamina.

Detailed examinations of the chronological progression of separated quantities of winnowings and lamina, using a suitable sensor, have revealed the following:

The overall separation rates are often unstable with respect to a nominal value, such that in these unstable phases too few winnowings are separated, and the product quality therefore drops when namely separation drops below the nominal value, or too great a proportion of lamina is lost for manufacturing when separation rises above the nominal value and lamina are therefore separated out as winnowings.

In phases of stable separating in the overall quantity, it is not possible to respond to naturally varying winnowing proportions in the tobacco material supplied, i.e. the separation rate cannot be retro-adjusted.

The separation setting on rod machines as set forth in the prior art is also not suitable for rapid intervention, the manufacturing process generally has to be interrupted to change the basic setting, in order to change the separating process, i.e. the means of separating the winnowings from the stream of tobacco particles. In the currently common systems, for instance, when using an impact metal sheet as the separator element, the machine has to be stopped and the position of the impact metal sheet changed by means of its fixing screws. This interruption, however, disrupts the continuity of manufacture, and it is not possible to check the changed separation in the minutes following the adjustment, since the result cannot reflect the value for continuous production.

This applies even when the winnowings are continually monitored using the sensor as set forth in DE 199 48 559 C1.

SUMMARY OF THE INVENTION

The invention is therefore based on the object of providing a method and a device for adjusting the selecting out of winnowings in the manufacture of smokable products, in which disadvantages mentioned above do not arise. In particular, the intention is to propose a method and a device which can optimally set the separating process at short notice and without interrupting the production process.

This object is solved by a method for adjusting the selecting out of winnowings in the manufacture of smokable products, in particular cigarettes, wherein the current size distribution of a stream of tobacco particles passing a measuring point, per unit of time, is detected and is compared with a settable nominal size distribution, wherein an arrangement for separating the winnowings is continually adjusted, depending on the result of said comparison, and by a device for adjusting the selecting out of winnowings in the manufacture of smokable products, in particular cigarettes, comprising a sensor for detecting the current size distribution of tobacco particles passing said sensor, per unit of time, an arrangement for inputting a nominal size distribution, an arrangement for comparing said current size distribution with said settable nominal size distribution, and an adjusting arrangement for setting an arrangement for separating the winnowings, depending on the output signal of said comparing arrangement.

Expedient embodiments are defined by the sub-claims.

The advantages achieved using the invention are initially based on using a sensor which detects the current size distribution of a stream of tobacco particles passing a measuring point, per unit of time. This can be a stream of separated winnowings or a stream of usable tobacco particles alone. Since, however, it is generally not possible to completely separate the winnowings from the usable tobacco particles, it is also possible to detect the size distribution of a stream containing both usable tobacco particles and winnowings.

This current size distribution detected, which in a stream of usable tobacco particles and winnowings consists of two partially overlapping size distributions, is compared to a corresponding, settable nominal size distribution, such that it is possible to determine from the result of this comparison how well the arrangement for separating the winnowings is set.

If the settings warrant changing, said arrangement is continually adjusted depending on the result of said comparison, until the current size distribution is again identical to the settable nominal size distribution.

A suitable sensor is described in DE 199 48 559 C1 and comprises a fine-beam light barrier which detects the dimensions of the tobacco particles in the transport direction, and from these dimensions determines the volume and/or mass flow rate of the tobacco particles passing the measuring point, from which the current size distribution can in turn be obtained.

If, in said sensor, two fine-beam light barriers are used, arranged in sequence in the transport direction of the tobacco particles, then the transport velocity can also be determined in addition to the dimensions of the tobacco particles, such that any changes in the transport velocity are automatically detected when determining the current size distribution.

Various methods are available for comparing the current size distribution and the nominal size distribution. Thus, for example, the peaks or the overall areas of the corresponding curves can be compared to each other, or the ratio between the size distributions for the winnowings and for the usable tobacco particles can be used for this purpose.

To adjust the arrangement for separating the winnowings, the spatial position of the various relevant separator units for the winnowings is expediently adjusted. In accordance with a preferred embodiment, an impact metal sheet serves as a separator unit and is continually adjusted by an electric motor, in particular a servo or step motor.

The electric motor can be attached directly to the impact metal sheet or it can be coupled to the impact metal sheet via Bowden wire connections, the impact metal sheet in turn being biased into a defined position via springs. The electric motor adjusts the impact metal sheet via the Bowden wire connections, against the bias force of the springs, thus pre-setting a defined nominal position.

As an alternative to this, it is also possible to intervene in the pneumatic separation of the winnowings from the usable tobacco particles, for example by varying the stream quantity and/or the pressure of the corresponding stream of air.

Lastly, it is also possible to adjust the velocity of the conveying medium for the stream of tobacco particles to the result of the comparison, wherein cylinders, belts or streams of air are available as conveying media for the stream of tobacco particles. The velocity of the cylinders and belts is changed mechanically by controlling the corresponding drive motors, while when using air as the conveying medium, the velocity of the stream of air is adjusted by changing the stream quantity and/or the pressure.

The type of intervention in the separating process depends of course on the cigarette manufacturing machine being used and on the separating technology.

In each case, the result is a very simple adjusting mechanism which only intervenes in the separating process of the cigarette manufacturing machine, automatically and without otherwise influencing the machine; in particular, it is no longer necessary to switch off the machine and manually change the basic setting of the separating process.

The nominal value for the size distribution can be pre-set on the basis of past experience. As an alternative to this, however, a sort of automatic calibration is also possible using the adjusting circuit described, if the optimum nominal value is determined by the adjusting method itself.

To this end, separation is for example varied, i.e. the impact metal sheet serving as a separating unit is for example moved in both directions and the change in the ratio of the size distribution (mass flow rate) of the winnowings to the size distribution (mass flow rate) of the usable tobacco particles is observed over a certain period of time. Since the intention, for example when detecting a stream of winnowings, is to work towards a situation where usable tobacco particles, i.e. tobacco particles below a certain mass, are no longer present, the system can automatically adjust the separating unit towards a nominal value which comes even closer to this optimum.

BRIEF DESCRIPTION OF THE DRAWINGS

In the following, the invention is explained in more detail on the basis of example embodiments and by referring to the enclosed, schematic drawings, which show.

DETAILED DESCRIPTION OF THE PREFERRED EMBODIMENTS

Figure 1:
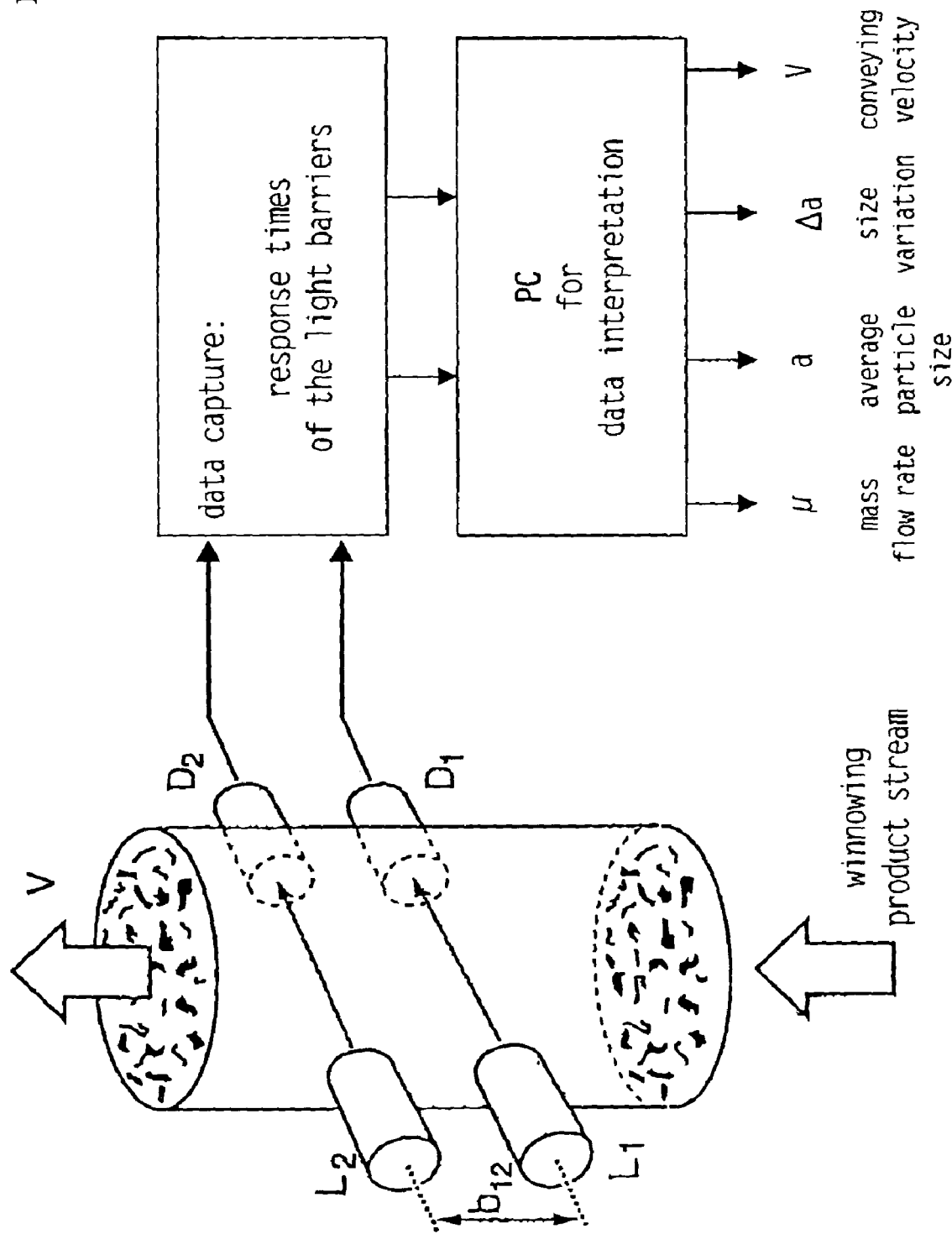
FIG. 1 a schematic representation of a sensor for a winnowing stream.

The sensor shown in FIG. 1, for detecting the current size distribution of the stream of tobacco particles is taken from DE 199 48 559 C1, whose disclosure is also incorporated into the present patent application.

As already mentioned above, when manufacturing cigarettes in the cigarette machine, the incoming tobacco stream is sifted. Only sufficiently fine tobacco material is built into the tobacco rod, while the remaining proportion of coarser material represents winnowings which are outputted at an output port of the cigarette machine and, conveyed by air, centrally collected to be further processed.

The winnowings are transported along this path through the conveying pipe shown in FIG. 1, said pipe simultaneously serving as a sensor pipe. This sensor pipe can be situated at a suitable point in the cigarette machine, on the conveying path for the winnowings, where enough space is available.

Two fine-beam light barriers are arranged on said sensor pipe, comprising a light source $L_1$, $L_2$ on one side of the sensor pipe and a detector $D_1$, $D_2$ on the opposite side of the sensor pipe. The measuring beam runs centrically through the pipe cross-section. The velocity of the winnowing product stream is indicated by the letter V, and the transport direction by the two arrows.

When, in accordance with normal conditions, the winnowing particle dimensions averaged over the longitudinal and transverse dimension measure 2 mm, and the measuring light beams of the two fine-beam light barriers have a diameter of 0.1 mm, then the dimensions of the tobacco particles flying past in the transport direction can be determined from the response time of each light barrier, i.e. from its eclipse time. From these dimensions, and using a calibration process which takes into account the density and the mean value of the particle sizes, a value can be determined for the average particle size, the mass flow rate, and the size variation.

The two light barriers are attached in the sensor pipe in sequence at a short distance from each other, such that the particle velocity V can be directly determined and indicated in the sensor itself, from the difference in time between the response signals of the two light barriers. The particle sensor thus becomes autark, i.e. independent of other measuring devices.

The size distribution of the winnowing stream can thus be determined from the data obtained, indicated in FIG. 1, said stream generally having two peaks, namely one for the winnowings and another for the usable tobacco particles still contained in the winnowing product stream despite the separation performed.

Figure 2:
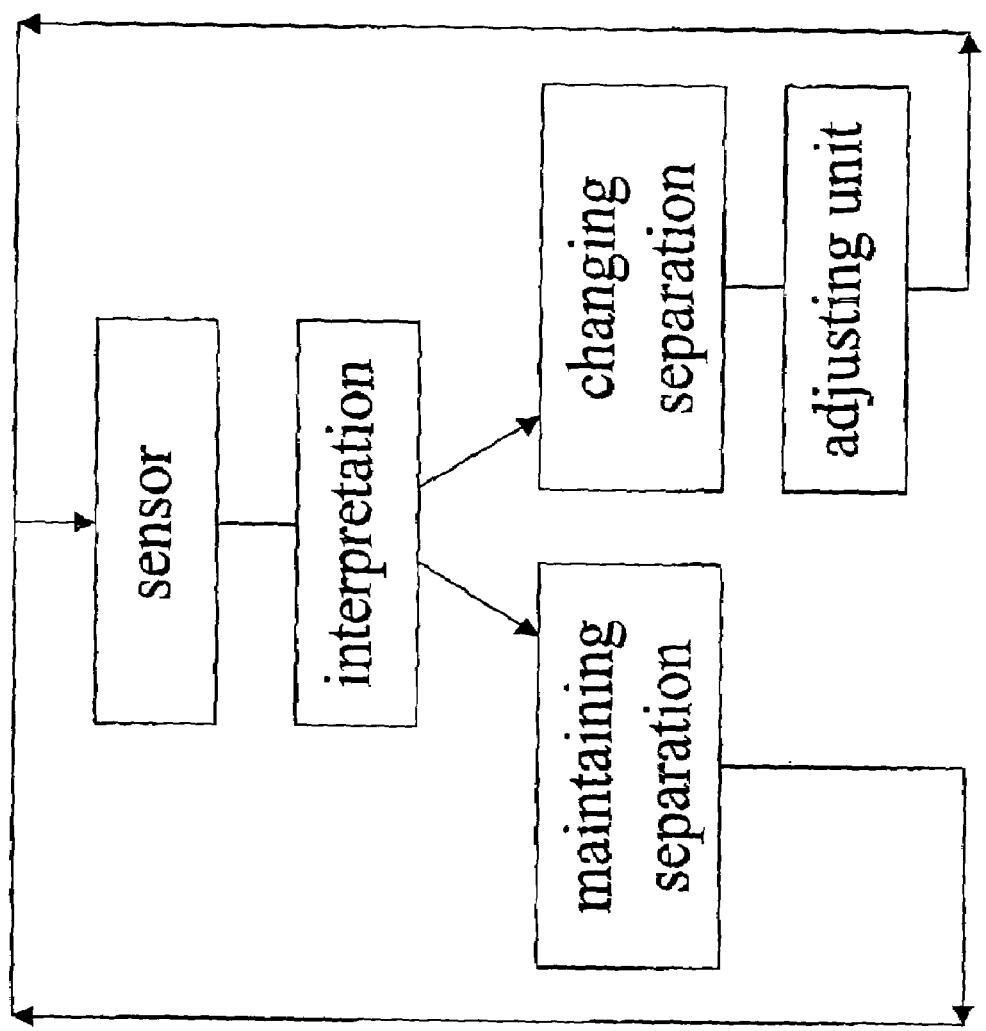
FIG. 2 a representation of the basic design of the adjusting circuit.

This or these two size distribution(s) currently determined by the sensor is/are supplied to the adjusting circuit shown in FIG. 2, which interprets it/them in a way still to be explained and compares it/them to a settable nominal size distribution. Depending on the result of this comparison, either the separating process is intervened in, i.e. separation is changed, or separation is left unchanged. If separation is changed, a corresponding signal is supplied to the adjusting unit of the separating unit in order to change its setting, which in turn influences the separating process.

The "interpretation" indicated in FIG. 2 also includes inputting a nominal value for the or for each size distribution, which can be either manually or automatically changed.

For self-adjusting in said adjusting process, the two size distributions—for the usable tobacco particles still contained in the winnowing product stream despite the application on the one hand, and the winnowing product stream on the other—are compared to each other, and an adjusting signal is outputted which adjusts the adjusting unit towards a reduction of the proportion of usable tobacco particles, i.e. towards a reduction of said size distribution.

A new measurement is then taken, and another adjustment made, until a nominal value is finally reached which corresponds to the optimum separation possible under the conditions present.

Figure 3:
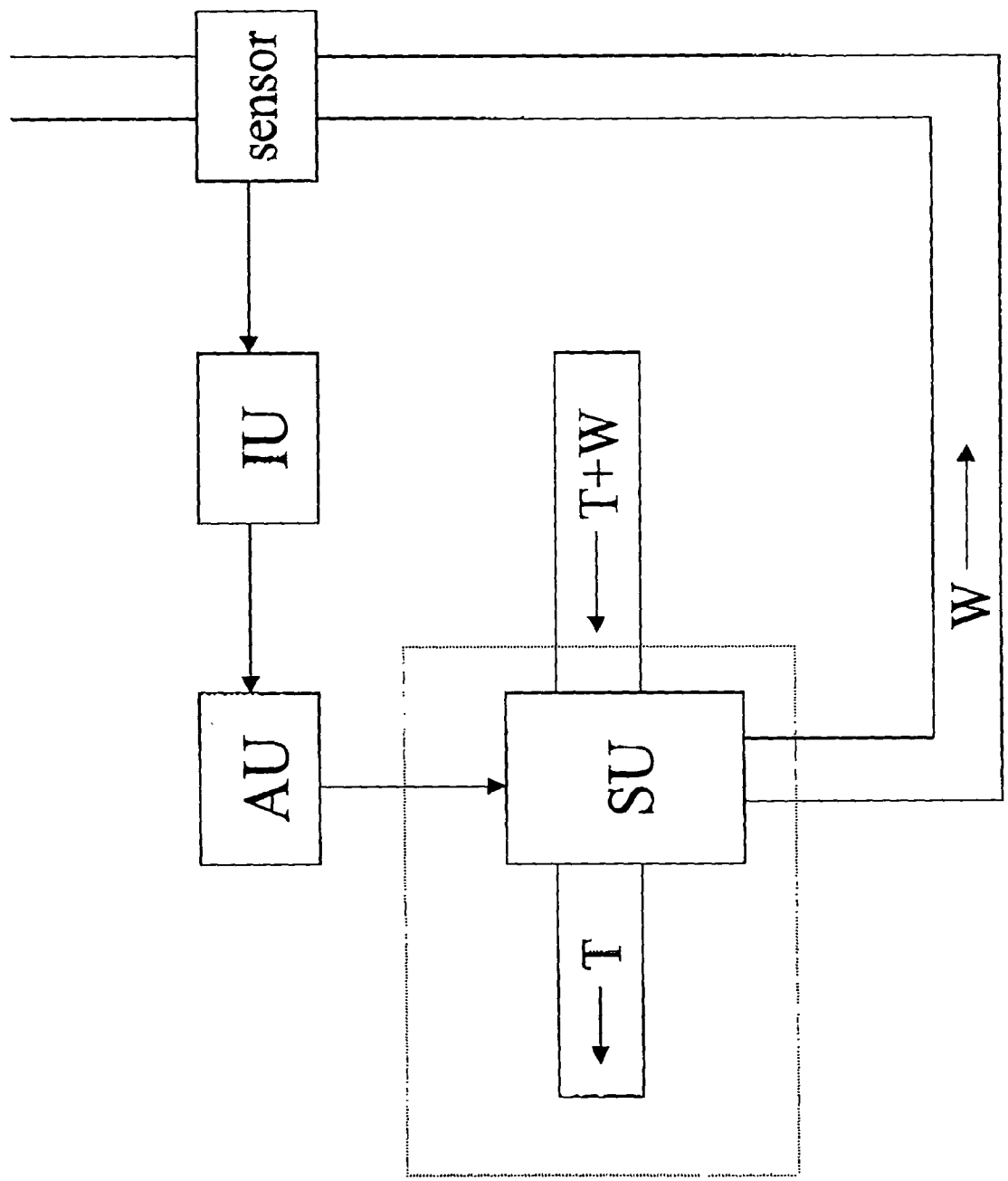
FIG. 3 a representation of the flow of material and the flow of data.

FIG. 3 shows the flow of data and material of a cigarette machine situated in the dotted rectangle. A stream of usable tobacco particles and winnowings T+W is supplied to said cigarette machine and separated in the settable separation unit SU into a stream T of usable tobacco particles and a stream W of winnowings.

This separation should preferably be such that the stream W contains only winnowings and the stream T contains only usable tobacco particles. In practice, however, this is generally not possible.

The separation unit SU has the design known from the prior art and is set to an appropriate value for separating the winnowings, depending on the type of cigarette machine used.

The stream T of usable tobacco particles is transported to the rod manufacturing (not shown) while the stream W of winnowings is conveyed out of the cigarette machine and supplied for example to a collecting point where it can be conditioned, possibly including another cutting process. This recovered proportion can then be re-supplied to the cigarette manufacturing.

The sensor shown in FIG. 3 is a fine-beam light barrier as set forth in German patent DE 199 48 559 C1, comprising two light beams (see FIG. 1) arranged on the path for pneumatically transporting the winnowings, generally including a small proportion of usable tobacco particles, in order to detect the size distribution of the separated winnowings and possibly also of the usable tobacco particles still present.

The readings, i.e. the current size distribution or also (see FIG. 1) the mass flow rate distribution are passed to an interpretation unit IU in which the nominal value and actual value are also compared as described.

If a change in the separation setting is necessary, the interpretation unit IU forwards a corresponding request to the adjusting unit AU, which—depending on the separating mechanism used and therefore the machine employed—adjusts the adjusting means which are normally used for the basic settings for separation.

As already explained above, various measures known from the prior art are available for separating the winnowings from the stream of usable tobacco particles, including in particular pneumatic measures for separating the stream of tobacco particles into two fractions. This separation can be influenced by influencing the stream of air, for example the air quantity, air pressure and/or air velocity.

The stream quantity can for example be varied in a particularly simple way by changing the stream cross-section, resulting in a very simple adjusting mechanism.

Furthermore, it is also possible to adjust the velocity of the conveying medium for the stream of tobacco particles to the result of interpretation, i.e. for example cylinders, belts or streams of air employed to pneumatically transport tobacco particles. Air quantity, air pressure and/or air velocity can in turn be influenced here too, which also results in a very simple adjusting mechanism when changing the stream cross-section.

These two separating mechanisms, possible in principle, are not shown in the drawings, since in accordance with a preferred embodiment, an impact metal sheet is used as the separating unit, such as is very often employed for separating winnowings. A corresponding embodiment is shown in FIG. 4.

Figure 4:
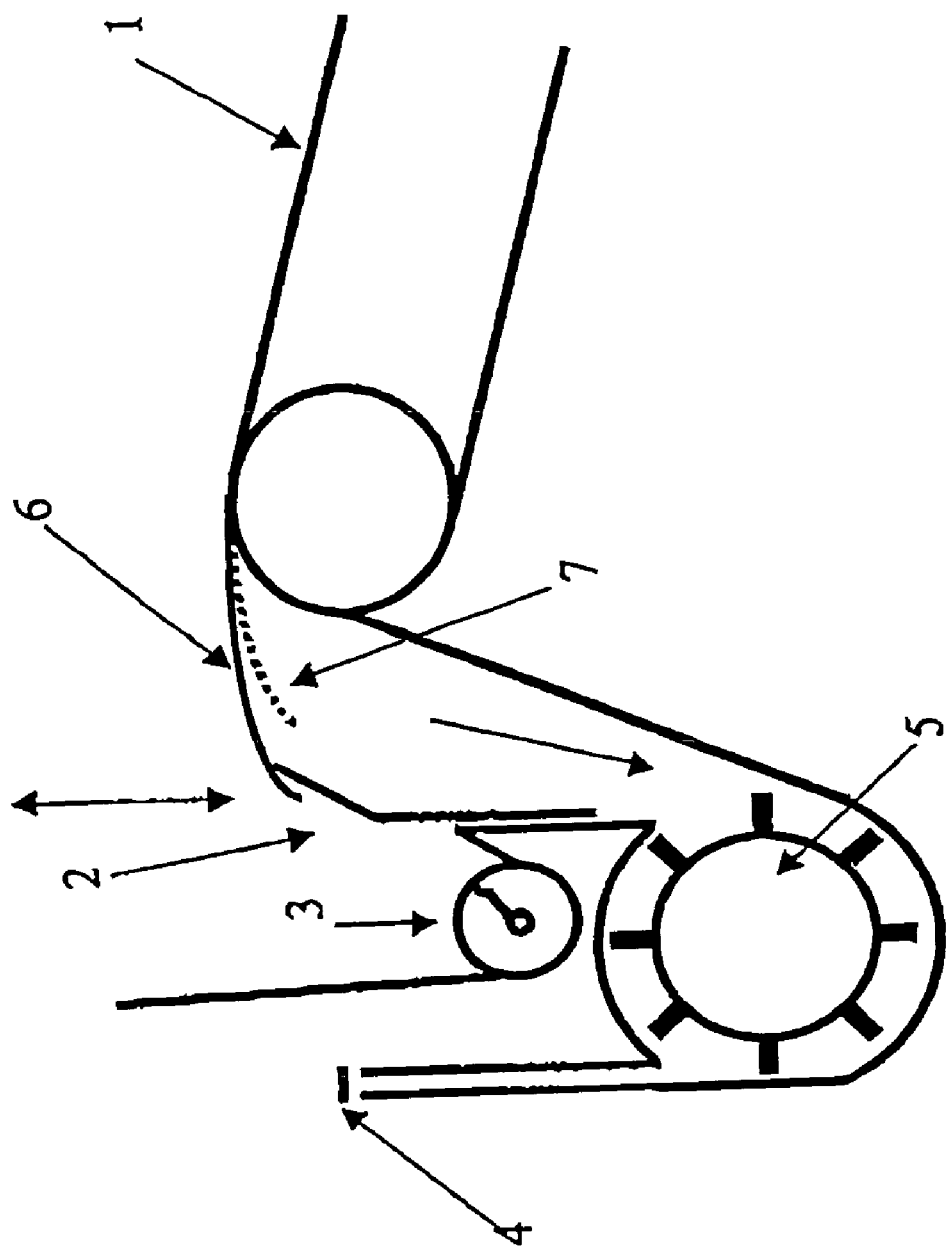
FIG. 4 a representation of a particularly preferred separating unit, namely an impact metal sheet.

A conveyor belt 1 conveys cut tobacco into the spreader of a cigarette rod machine which, at the left-hand end of the conveyor belt in accordance with the representation in FIG. 4, describes a ballistic curve which is influenced by the final velocity of the conveyor belt at the point at which the tobacco particles are released.

After leaving the conveyor belt 1, two substantial forces act on the tobacco particles: due to their kinetic energy, the tobacco particles continue to move in the direction of the conveyor belt, and they are simultaneously accelerated downwards by gravity, such that the overall result is a movement curve of the now free tobacco particles in the manner of a ballistic parabola.

The shape of said ballistic parabola is also additionally influenced by a force exerted by a suction belt 4 to which a partial vacuum is applied, such that the lighter of the tobacco particles leaving the conveyor belt 1 are deflected downwards more strongly than the heavier ones by the stream of conveying air moving towards the suction belt 4 in the direction of the arrow due to the partial vacuum. As a result, the lighter tobacco particles impact against an impact metal sheet 2, fall downwards and are conveyed to the suction belt 4 by the partial vacuum, assisted by a conveying cylinder 5. The trajectory of these lighter usable tobacco particles is indicated by the dotted ballistic parabola 7.

The heavier winnowings, through their higher kinetic energy, surmount the upper edge of the impact metal sheet 2 and fall into a conveying screw 3 such as is indicated by the corresponding, continuous ballistic parabola 6; they are transported away by the conveying screw 3 and disposed of pneumatically, out of the machine.

Positioned in said pneumatic transporting path, at a suitable point and as near as possible to the spreader and/or cigarette rod machine, is the sensor shown in FIG. 1, which detects the size distribution of the tobacco particles, in this case therefore the winnowings.

It is possible to intervene in the actual separating process by adjusting the height of the impact metal sheet 2, indicated by the double arrow above the ballistic parabola 6, and therefore to determine via the adjustment explained which particle sizes are disposed of as winnowings and which particle sizes enter the tobacco rod for manufacturing the cigarette.

Ideally, the stream of winnowings contains only winnowings; however, even when the separating process is optimally set, this is only rarely possible, such that the sensor generally measures not only the single size distribution for the winnowings, but rather a double distribution for the size distribution of the winnowings and the size distribution of the usable tobacco particles still present.

As mentioned, it is possible to determine a deviation from the desired value, and accordingly intervene in the separating process, by comparing the or each current size distribution, as detected by the sensor, with the inputted nominal value(s) for the size distribution(s).

For this purpose, the two size distributions can be directly compared to each other, or however just the heights of their peaks can be correlated.

It is also possible to compare the ratio of the two current size distributions to a corresponding nominal value which—as mentioned above—can also be inputted automatically.

The impact metal sheet 2 can be adjusted, as indicated by the double arrow, by a servo or step motor which is fixed directly to the impact metal sheet 2 and activated by the adjusting unit AU, depending on the output signal of the sensor (see FIG. 3).

As an alternative to this, it is also possible to connect an adjusting motor, in particular a servo or step motor, to the impact metal sheet 2 via Bowden wire connections (not shown), said impact metal sheet 2 being biased via springs 4 in order to adjust it downwards, in accordance with the representation in FIG. 4. The servo or step motor thus pulls the impact metal sheet 2 upwards, overcoming the biasing force of the springs, such that the upper end of the impact metal sheet 2 enters the transport path of the tobacco particles, formed by the two ballistic parabolas 6, 7, and thus separates the winnowings.

In the foregoing description, preferred embodiments of the invention have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A method for continually adjusting the separating out of winnowings from usable tobacco particles during the manufacture of smokable products, comprising:
    a) detecting the current size distribution of a stream of tobacco particles passing a measuring point, per unit of time; and
    b) comparing the size distribution with a settable nominal size distribution; and
    c) continually adjusting an arrangement for separating the winnowings, depending on the result of said comparison.

2. The method as set forth in claim 1, wherein said smokable products are cigarettes.

3. The method as set forth in claim 1, wherein the current size distribution of a stream of separated winnowings, of a stream of usable tobacco particles and winnowings or of a stream of usable tobacco particles alone is detected and compared with a corresponding, settable nominal size distribution.

4. The method as set forth in claim 1, wherein said current size distribution is determined by detecting the dimensions of the tobacco particles in the transport direction at said measuring point.

5. The method as set forth in claim 4, wherein the dimensions of the tobacco particles are detected using a fine-beam light barrier.

6. The method as set forth in claim 5, wherein the volume or the mass flow rate of the tobacco particles passing the measuring point is determined by detecting the dimensions of the tobacco particles in the transport direction.

7. The method as set forth in claim 1, wherein the current size distribution and the nominal size distribution are compared on the basis of their peaks or the overall area of the corresponding curve.

8. The method as set forth in claim 1, wherein the current size distribution and the nominal size distribution are compared on the basis of the ratio between the size distributions for the winnowings and for the usable tobacco particles.

9. The method as set forth in claim 1, wherein the spatial position of the arrangement for separating the winnowings is adjusted, depending on the result of said comparison.

10. The method as set forth in claim 9, wherein an impact sheet serves as the arrangement for separating the winnowings and is continually adjusted using an electric motor.

11. The method as set forth in claim 10, wherein said impact sheet is an impact metal sheet.

12. The method as set forth in claim 10, wherein said electric motor is a servo or step motor.

13. The method as set forth in claim 10, wherein said electric motor is directly attached to said impact sheet.

14. The method as set forth in claim 10, wherein said electric motor is coupled to said impact metal sheet via Bowden wire connections, said impact sheet being biased into a defined position via springs.

15. The method as set forth in claim 9, wherein a stream of air serving to separate an initial stream of tobacco particles into the usable particles and winnowings is adjusted, depending on the result of the comparison.

16. The method as set forth in claim 15, wherein the stream quantity or the pressure of the stream of air is adjusted.

17. The method as set forth in claim 9, wherein the velocity of a conveying medium for the stream of tobacco particles is adjusted, depending on the result of the comparison.

18. The method as set forth in claim 17, wherein cylinders, belts or streams of air are used as said conveying medium.

19. The method as set forth in claim 18, wherein the velocity of the stream of air serving as the conveying medium for winnowings is adjusted by changing the stream quantity or the pressure.

20. The method as set forth in claim 1, wherein the nominal size distribution is determined by detecting the change in the ratio of the size of the winnowings to the size distribution of the usable tobacco particles and optimizing said ratio by adjusting the arrangement for separating the winnowings.

21. A method for separating winnowings in a stream containing tobacco particles during the manufacturing of cigarettes comprising:
generating a size distribution of a tobacco particle stream;
comparing said size distribution with an optimal size distribution;
continually adjusting said size distribution of said tobacco particle stream using a separation unit for separating winnowings the functioning of which is based upon said comparing step.

22. The method of claim 21 wherein said generating of said size distribution of said tobacco particle stream is conducted on a tobacco particle stream of winnowings and finer lamina tobacco particles.

23. The method of claim 21 wherein said size distribution is created by detecting an average individual particle size of said tobacco particle stream.

24. The method of claim 23 wherein said generating of said size distribution is completed using a fine beam light barrier.

25. The method of claim 21 wherein said size distribution of said tobacco particle stream and said optimal size distribution are compared on the basis of an area of each individual size distribution.

26. The method as set forth in claim 21 wherein said comparing step is conducted based on a comparison of the peaks of each of said size distributions.

27. The method of claim 21 wherein said size distribution of a tobacco particle stream is compared to said optimal size distribution on the basis of a ratio between a size distribution for winnowings and a size distribution of larger tobacco lamina particles.

28. The method of claim 21 wherein said separation unit is an impact sheet and further comprising adjusting said impact sheet to separate particles in said tobacco particle stream.

29. The method of claim 28 further comprising biasing said impact sheet into a pre-defined position for proper separation of said tobacco particle stream.

30. A method of separating tobacco particles during cigarette making from a particle stream, comprising:
measuring a size distribution of a tobacco particle stream containing winnowings and finer tobacco particles;
comparing said measured size distribution to an optimal size distribution;
continually adjusting an impact sheet within a cigarette maker, said impact sheet located within said particle stream;
separating finer tobacco particles in said particle stream from winnowings by said continual adjustment of said impact sheet.

* * * * *